(12) United States Patent
Marsilje et al.

(10) Patent No.: US 7,816,542 B2
(45) Date of Patent: Oct. 19, 2010

(54) COMPOUNDS AND COMPOSITIONS AS TPO MIMETICS

(75) Inventors: Thomas Marsilje, San Diego, CA (US);
Wenshuo Lu, San Diego, CA (US);
Phillip B. Alper, San Diego, CA (US);
Daniel Mutnick, San Diego, CA (US);
Yun He, Shanghai (CN)

(73) Assignee: IRM LLC, Hamilton (BM)

( * ) Notice: Subject to any disclaimer, the term of this patent is extended or adjusted under 35 U.S.C. 154(b) by 101 days.

(21) Appl. No.: 12/063,350

(22) PCT Filed: Aug. 15, 2006

(86) PCT No.: PCT/US2006/031986

§ 371 (c)(1),
(2), (4) Date: Feb. 8, 2008

(87) PCT Pub. No.: WO2007/022269

PCT Pub. Date: Feb. 22, 2007

(65) Prior Publication Data

US 2008/0194668 A1    Aug. 14, 2008

Related U.S. Application Data

(60) Provisional application No. 60/708,438, filed on Aug. 15, 2005.

(51) Int. Cl.
*A61K 31/404* (2006.01)
*C07D 209/10* (2006.01)

(52) U.S. Cl. ...................................... 548/511; 514/415

(58) Field of Classification Search .................. 548/511
See application file for complete search history.

(56) References Cited

U.S. PATENT DOCUMENTS

| 4,026,891 | A |   | 5/1977  | Austel et al. |
|-----------|---|---|---------|---------------|
| 4,361,563 | A |   | 11/1982 | Austel et al. |
| 4,522,808 | A | * | 6/1985  | Jacquet et al. ................ 424/59 |
| 5,502,071 | A | * | 3/1996  | Gange ........................ 514/415 |
| 6,486,153 | B1 | * | 11/2002 | Castro Pineiro et al. ......... 514/217.08 |
| 6,699,862 | B1 | * | 3/2004  | Goldstein et al. ........ 514/235.2 |
| 6,787,550 | B1 |   | 9/2004  | Farina et al. |
| 7,126,009 | B2 | * | 10/2006 | Li et al. ...................... 548/508 |
| 2004/0138287 | A1 | * | 7/2004 | Barth et al. .................. 514/419 |
| 2005/0038095 | A1 |   | 2/2005 | Farina et al. |

FOREIGN PATENT DOCUMENTS

| JP | 2306916 | 12/1990 |
| WO | WO99/41241 | 8/1999 |
| WO | WO-01/02388 A1 * | 1/2001 |
| WO | WO 2005/009993 | 2/2005 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Dai et al., Tetrahedron Letters, 2001, 42(31), pp. 5275-5278.*
Watanabe et al., Chemistry Letters, (Apr. 16, 2005), 34(5), pp. 718-719.*
Rutherford et al., Journal of the American Chemical Society, (2002), 124(51), pp. 15168-15169.*
Le Breton et al., CA 124:302280, 1996.*
Otto et al., CA 102:163182, 1985.*
Dann et al., CA 75:129600, 1971.*
An English translation of JP 02-306916, Dec. 1990.*
Nishi, Takao et al., "Preparation of benzothiazoles and benzimidazoles as blood platelet aggregation inhibitors", retrieved from STN Database accession No. 1991:207259 abstract and JP 02 306916 A (Otsuka Pharmaceutical Co., Ltd.,; Dec. 20, 1990.
Syed Abuzar et. al., "Synthesis of Benzimidazoles as Potential Anthelminthics", Arch. Pharm., 315, 866-871, (1982).
Rangarajan M. et al., "Topoisomerase I Inhibition and Cytotoxicity of 5-Bromo- and 5-Phenylterbenzimidazoles", Bioorganic & Medicinal Chemistry, 8, 2591-2600, (2000).
Rangarajan M. et al., "2"-Substituted 5-Phenylterbenzimidazoles as Topoisomerase I Inhibition Poisons", Bioorganic & Medicinal Chemistry, 8, 1371-1382, (2000).

* cited by examiner

*Primary Examiner*—Laura L. Stockton
(74) *Attorney, Agent, or Firm*—Daniel E. Raymond; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated TPO activity, particularly diseases or disorders that involve thrombocytopenia.

6 Claims, No Drawings

COMPOUNDS AND COMPOSITIONS AS TPO MIMETICS

CROSS-REFERENCE TO RELATED APPLICATIONS

This application is a 371 U.S. national phase application of international application number PCT/US2006/031986 filed 15 Aug. 2006, which application claims priority to U.S. provisional patent application No. 60/708,438, filed 15 Aug. 2005. The full disclosure of this application is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated TPO activity, particularly diseases or disorders that involve thrombocytopenia.

2. Background

Megakaryocytes are bone marrow-derived cells, which are responsible for producing circulating blood platelets. Thrombopoietin (TPO), a hematopoietic cytokine, supports the process of cellular proliferation and differentiation of hematopoietic stem cells and is necessary for the regulation of megakaryocytes.

The novel compounds of this invention, as TPO mimetics, are useful in treating diseases or conditions that anticipate and/or result in a decrease in blood or blood platelets including, but not limited to, radiation therapy, chemotherapy, immune therapy, cancers, viral infections, and transplants such as bone marrow and stem cell transplants.

SUMMARY OF THE INVENTION

In one aspect, the present invention provides compounds of Formula I:

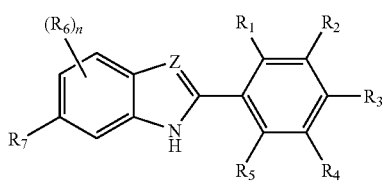

in which:

n is selected from 0, 1, 2 and 3;

Z is selected from N and $CR_8$; wherein $R_8$ is selected from hydrogen, halo, $C_{1-6}$alkyl, halo-substituted-$C_{1-6}$alkyl; wherein any alkyl of $R_8$ can optionally have a methylene replaced by an atom or group selected from —S(O)$_{0-2}$—, —C(O)—, —NR$_9$— and —O—; wherein $R_9$ is selected from hydrogen and $C_{1-6}$alkyl;

$R_1$, $R_2$, $R_4$ and $R_5$ are independently selected from hydrogen, halo, hydroxy, cyano, nitro, —XNR$_9$R$_{10}$, $C_{1-6}$alkyl, halo-substituted-$C_{1-6}$alkyl, $C_{1-6}$alkoxy and halo-substituted-$C_{1-6}$alkoxy; wherein X is selected from a bond and $C_{1-6}$alkylene; and $R_9$ and $R_{10}$ are independently is selected from hydrogen and $C_{1-6}$alkyl;

$R_3$ is selected from hydrogen, $C_{1-6}$alkyl, $C_{3-8}$heterocycloalkyl, $C_{5-10}$heteroaryl, —OS(O)$_2$R$_{11}$, —NR$_{11}$S(O)$_2$R$_{12}$, —NR$_{11}$C(O)R$_{12}$, —NR$_{11}$C(O)NR$_{11}$R$_{12}$, —NR$_{11}$C(O)C(O)OR$_{12}$, —NR$_{11}$C(O)OR$_{12}$, —OC(O)NR$_{11}$R$_{12}$, —C(O)OR$_{11}$, —C(O)R$_{13}$, —NR$_{11}$R$_{12}$, NR$_{11}$R$_{13}$, —S(O)$_2$NR$_{11}$R$_{12}$ and —C(O)NR$_{11}$R$_{12}$; wherein $R_{11}$ and $R_{12}$ are independently selected from hydrogen, $C_{1-6}$alkyl, halo-substituted-$C_{1-6}$alkyl, $C_{1-6}$alkoxy, cyano-$C_{1-6}$alkyl, hydroxy-$C_{1-6}$alkyl and $C_{1-6}$alkyl substituted with —NR$_9$R$_{10}$; $R_{13}$ is $C_{3-8}$heterocycloalkyl optionally substituted with 1 to 3 $C_{1-6}$alkyl radicals; wherein any heterocycloalkyl or heteroaryl of $R_3$ can be optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl and halo-substituted-$C_{1-6}$alkoxy;

$R_6$ is selected from halo and $C_{1-6}$alkyl; and $R_7$ is selected from halo, cyano, $C_{1-6}$alkyl, $C_{2-6}$alkenyl, $C_{2-6}$alkynyl, halo-substituted-$C_{1-6}$alkyl, $C_{6-10}$aryl, $C_{5-10}$heteroaryl, $C_{3-8}$heterocycloalkyl and $C_{3-12}$cycloalkyl; wherein any alkyl, alkenyl, alkynyl, aryl, heteroaryl, cycloalkyl or heterocycloalkyl is optionally substituted by 1 to 5 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, —NR$_{14}$R$_{15}$, —XOR$_{14}$, —S(O)$_2$R$_{14}$, $C_{3-12}$cycloalkyl, $C_{3-8}$heterocycloalkyl, $C_{6-10}$aryl and $C_{3-8}$heteroaryl; wherein X is a bond or $C_{1-6}$alkylene and $R_{14}$ and $R_{15}$ are independently selected from $C_{1-6}$alkyl, cyano-$C_{1-6}$alkyl, hydroxy-$C_{1-6}$alkyl, halo-substituted-$C_{1-6}$alkyl and halo-substituted-$C_{1-6}$alkoxy; wherein any aryl, heteroaryl, cycloalkyl and heterocycloalkyl substituents of $R_7$ are optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl and halo-substituted-$C_{1-6}$alkoxy; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease or condition in an animal in which increased blood platelet levels, can inhibit or ameliorate the pathology and/or symptomology of the disease or condition, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease or condition in an animal in which decreased blood platelet levels, contributes to the pathology and/or symptomology of the disease or condition.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Thrombopoietin (TPO)" is also known in the art as c-Mpl ligand, mpl ligand, megapoietin, and megakaryocyte growth and development factor.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of thrombocytopenia. Thrombocytopenia can be broadly interpreted as any decrease in the number of blood platelets below what is considered normal or desired for a healthy individual.

In one embodiment, with reference to compounds of Formula I, are compounds of Formula Ia:

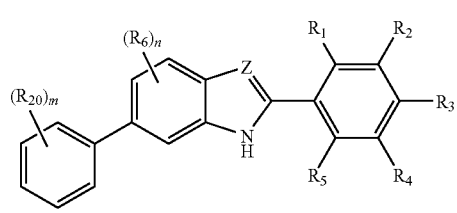

Ia in which:

n is selected from 0, 1, 2 and 3;

m is selected from 0, 1, 2, 3, 4 and 5;

Z is selected from N and CR$_8$; wherein R$_8$ is selected from hydrogen, halo, $C_{1-6}$alkyl, halo-substituted-$C_{1-6}$alkyl; wherein any alkyl of R$_8$ can optionally have a methylene replaced by an atom or group selected from —S(O)$_{0-2}$—, —C(O)—, —NR$_9$— and —O—; wherein R$_9$ is selected from hydrogen and $C_{1-6}$alkyl;

R$_1$, R$_2$, R$_4$ and R$_5$ are independently selected from hydrogen, halo, hydroxy, nitro, —XNR$_9$R$_{10}$, $C_{1-6}$alkyl, halo-substituted-$C_{1-6}$alkyl; wherein X is selected from a bond and $C_{1-6}$alkylene; and R$_9$ and R$_{10}$ are independently is selected from hydrogen and $C_{1-6}$alkyl;

R$_3$ is selected from —XCOOR$_9$, —XCONR$_9$R$_{10}$, —NR$_{11}$S(O)$_2$R$_{12}$, —S(O)$_2$NR$_{11}$R$_{12}$, —NR$_{11}$C(O)R$_{12}$, —NR$_{11}$C(O)NR$_{11}$R$_{12}$, —NR$_{11}$C(O)C(O)OR$_{12}$ and —NR$_{11}$C(O)OR$_{12}$; wherein X is selected from a bond and $C_{1-6}$alkylene; and R$_9$ and R$_{10}$ are independently is selected from hydrogen and $C_{1-6}$alkyl;

R$_6$ is selected from halo and $C_{1-6}$alkyl; and

R$_{20}$ is selected from halo and $C_{1-6}$alkyl.

In another embodiment, R$_6$ is fluoro and R$_{20}$ is selected from fluoro, methyl and butyl.

In another embodiment, R$_3$ is selected from carboxyl, amino-carbonyl, amino-sulfonyl, methyl-sulfonyl-amino and amino; and R$_4$ is selected from hydrogen, hydroxyl, nitro and amino.

Preferred compounds of the invention are selected from 4-[6-(4-butyl-phenyl)-7-fluoro-1H-indol-2-yl]-benzoic acid; 4-[6-(4-butyl-phenyl)-7-fluoro-1H-indol-2-yl]-benzamide; 4-[7-fluoro-6-(4-fluoro-3-methyl-phenyl)-1H-indol-2-yl]-benzoic acid; 4-[7-fluoro-6-(4-fluoro-3-methyl-phenyl)-1H-indol-2-yl]-benzenesulfonamide; 4-[6-(4-butyl-phenyl)-3-ethyl-7-fluoro-1H-indol-2-yl]-2-hydroxy-benzoic acid; 4-[6-(4-butyl-phenyl)-7-fluoro-3-isopropyl-1H-indol-2-yl]-2-hydroxy-benzoic acid; 4-[6-(4-butyl-phenyl)-7-fluoro-1H-indol-2-yl]-2-hydroxy-benzoic acid; 4-[6-(4-butyl-phenyl)-7-fluoro-3-methyl-1H-indol-2-yl]-2-hydroxy-benzoic acid; 4-[6-(4-butyl-phenyl)-1H-benzoimidazol-2-yl]-benzoic acid; 4-[6-(4-butyl-phenyl)-1H-benzoimidazol-2-yl]-2-hydroxy-benzoic acid; N-{4-[6-(4-Butyl-phenyl)-7-fluoro-1H-indol-2-yl]-phenyl}-methanesulfonamide; N-{4-[6-(4-Butyl-phenyl)-7-fluoro-1H-indol-2-yl]-phenyl}-acetamide; N-{4-[6-(4-Butyl-phenyl)-7-fluoro-1H-indol-2-yl]-2-chloro-phenyl}-acetamide; 4-[6-(4-Butyl-phenyl)-7-fluoro-1H-indol-2-yl]-2-chloro-phenylamine; and 2-Amino-4-[6-(4-butyl-phenyl)-7-fluoro-1H-indol-2-yl]-benzoic acid.

Further preferred compounds of the invention are detailed in the Examples and Tables, infra.

Pharmacology and Utility

Thrombocytopenia can be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura, myelodysplastic syndrome (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in TPO, neutropenia, dendritic cell mobilization, proliferation, activation or differentiation.

TPO has significant therapeutic value in the treatment of patients with reduced platelet count. In particular patients with many types of cancer suffer thrombocytopenias because of myelosuppressive chemotherapy or radiation therapy which can cause an increase in the risk of bleeding and often limits the dose of chemotherapeutic agents that may be given to receiving intensive chemotherapy or bone marrow transplantation.

The compounds of this invention are useful in treating thrombocytopenia regardless of the factor or factors causing the condition. The compounds of this invention are also useful in treating thrombocytopenia when the causative factor or factors of the condition are unknown or have yet to be identified. The compounds of this invention are useful whenever a decrease in blood or blood platelets is anticipated including, but not limited to, transplant surgery, surgery, anesthesia prior to child birth and gut protection.

Because platelets (thrombocytes) are necessary for blood clotting and when their numbers are very low a patient is at risk of death from catastrophic hemorrhage, TPO mimetics of the invention have a useful application in the treatment of various hematological disorders, for example, diseases primarily due to platelet defects.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). The TPO mimetic compounds of the current invention are also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents.

Human dendritic cells have been shown to express the TPO receptor and TPO is a potent mobilizer of dendritic cells. The TPO mimetic compounds of the current invention are also useful as a vaccine adjuvant in that they increase the activity and mobility of dendritic cells. The pharmaceutically active compounds of this invention are useful as an immunological adjuvant, given in combination with an orally, transdermally or subcutaneously delivered vaccine and/or immunomodulator, by increasing the activity and mobility of dendritic cells.

TPO is known to have various effects including anti-apoptotic/survival effects on megakaryocytes, platelets and stem cells, and proliferative effects on stem cells and megakaryocytic cells. Therefore TPO and/or TPO mimetics of the invention, effectively increase the number of stem and progenitor cells so that there is synergistic effects when TPO is used in conjunction with other cytokines that induce differentiation.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which Z is N, can be prepared by proceeding as in the following Reaction Scheme I:

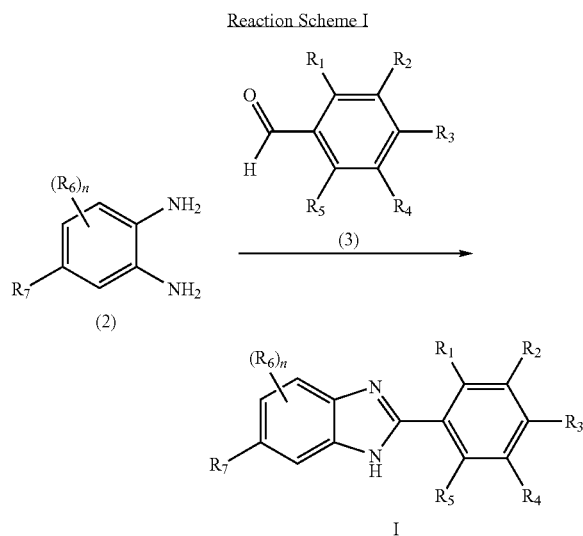

in which n and $R_1$ to $R_7$ are as defined in the Summary of the Invention. A compound of Formula I can be synthesized by reacting a compound of formula 2 with a compound of formula 3 in the presence of sodium hydrogen sulfite in a suitable solvent (for example, DMA, and the like). The reaction proceeds in a temperature range of about 100° C. to about 180° C. and can take up to about 24 hours to complete.

Compounds of Formula I, in which Z is $CR_8$, can be prepared by proceeding as in the following Reaction Scheme II:

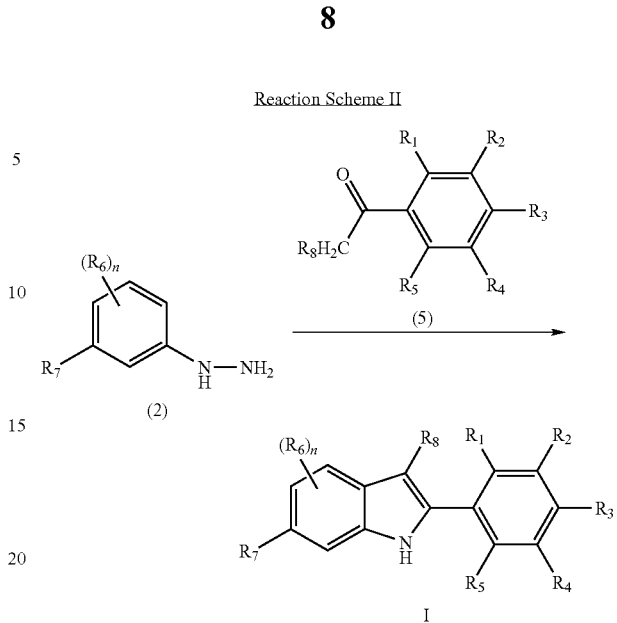

in which n and $R_1$ to $R_8$ are as defined in the Summary of the Invention. A compound of Formula I can be synthesized by reacting a compound of formula 2 with a compound of formula 5 in the presence of a suitable Lewis acid (for example, Zinc chloride, and the like) or protic acid (for example, HCl, and the like) in a suitable solvent (for example, acetic acid, ethanol, and the like). The reaction proceeds in a temperature range of about 80° C. to about 120° C. and can take up to about 72 hours to complete.

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
(a) that of reaction schemes I or II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

4-[6-(4-Butyl-phenyl)-7-fluoro-1H-indol-2-yl]-benzoic acid

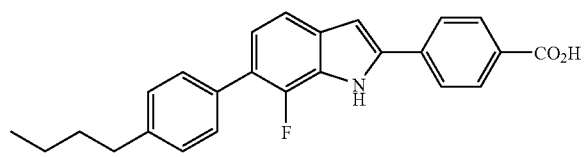

Step 1: 4-(6-Chloro-7-fluoro-1H-indol-2-yl)-benzoic acid methyl ester:

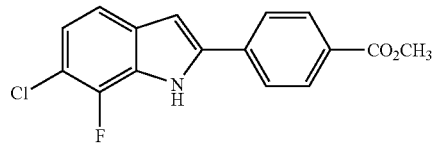

(3-Chloro-2-fluoro-phenyl)-hydrazine hydrochloride (Apollo Scientific, Ltd., 221 mg, 1.12 mmol) and 4-acetyl-benzoic acid methyl ester (200 mg, 1.12 mmol) are treated with anhydrous $ZnCl_2$ (382 mg, 2.81 mmol) and acetic acid (10 mL). The reaction is heated to 105° C. for 48 hours. After cooling to room temperature, the reaction is diluted with ethyl acetate and sequentially washed with $H_2O$ (5×) followed by saturated aqueous NaCl. The organics are then dried over $Na_2SO_4$ and filtered. After concentration, the crude product is purified by preparative RP LC-MS to give 4-(6-chloro-7-fluoro-1H-indol-2-yl)-benzoic acid methyl ester as an off-white solid: ESMS m/z 304.0 (M+H$^+$).

Steps 2 and 3: To a mixture of 4-(6-chloro-7-fluoro-1H-indol-2-yl)-benzoic acid methyl ester (37 mg, 0.122 mmol) from the previous step, 4-n-butylphenyl-boronic acid (43 mg, 0.244 mmol), and cesium carbonate (159 mg, 0.487 mmol) in dioxane (4 mL), is added CombiPhos-Pd6 palladium catalyst (Combiphos Catalysts Inc., 3 mg). The mixture is purged with $N_2$ for 5 minutes and heated at 120° C. for 7 hours in a sealed tube. After cooling to room temperature, the reaction is diluted with ethyl acetate and sequentially washed with 1 N HCl, $H_2O$, and saturated aqueous NaCl. The organics are then dried over $Na_2SO_4$, filtered, and concentrated. The resulting residue is treated with ethanol/$H_2O$ (2 mL/1 mL) followed by LiOH (26 mg, 0.609 mmol). This mixture is heated at 50° C. for 1 hour. After cooling to room temperature, the reaction is diluted with ethyl acetate and washed with 1 N aqueous HCl. The organic layer is dried over $Na_2SO_4$ and filtered. After concentration, the crude product is purified by preparative RP LC-MS to give 4-[6-(4-Butyl-phenyl)-7-fluoro-1H-indol-2-yl]-benzoic acid as a white solid: $^1$H NMR (400 MHz, Acetone-$d_6$) δ 11.13 (bs, 1H), 8.10-8.05 (m, 4H), 7.59 (d, 2H), 7.52 (d, 1H), 7.32 (d, 2H), 7.18-7.12 (m, 2H), 2.71 (t, 2H), 1.70-1.63 (m, 2H), 1.49-1.40 (m, 2H), 0.98 (t, 3H); ESMS m/z 388.2 (M+H$^+$).

Example 2

4-[6-(4-Butyl-phenyl)-7-fluoro-1H-indol-2-yl]-benzamide

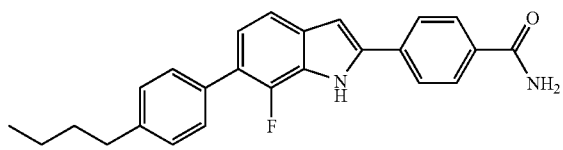

Step 1: (4'-Butyl-2-fluoro-biphenyl-3-yl)-hydrazine Hydrochloride

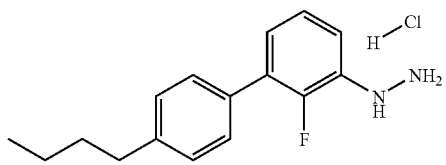

A mixture of dioxane (16 mL) and N-methylpyrrolidinone (8 mL) is deoxygenated by passing a stream of nitrogen through it for 15 minutes. A sample of 3-chloro-2-fluoroaniline (3 g, 20.6 mmol) is charged to a 250 mL round-bottom flask which is equipped with a screw-top adapter capable of sealing the vessel via a 3 way stopcock. The aniline is then treated with 4-butylphenylboronic acid (5.5 g, 30.9 mmol), cesium fluoride (7.82 g, 51.5 mmol) and bis-(tri-tert-butyl phosphiono) palladium (527 mg, 1.03 mmol). The flask is evacuated, back filled with nitrogen, and sealed. The flask is placed into an oil bath which has been preheated to 130° C. and stirred for 4 hours. After cooling, the reaction is filtered through a pad of celite which is subsequently rinsed with EtOAc. The organics are then removed by rotary evaporation. The crude reaction is diluted with water, and extracted with EtOAc. The phases are separated, and the organics are dried over MgSO$_4$, filtered, and concentrated. The resulting oil is diluted with diethyl ether and treated with an excess of a 4 M solution of HCl in dioxane. The resulting solid is collected, washed with diethyl ether, and dried to give 4'-butyl-2-fluoro-biphenyl-3-ylamine hydrochloride as a white solid: LC/MS calculated for [M+H]+ C16H19FN: 244.3, found: 244.2. A 0° C. mixture of 4'-butyl-2-fluoro-biphenyl-3-ylamine hydrochloride (5.4 g, 0.019 mol) in concentrated aqueous HCl (50 ml) is treated with the drop wise addition of sodium nitrite (1.3 g, 0.019 mol) in H$_2$O (20 ml) over 10 minutes. The resulting solution is stirred at 0° C. for 1 hour and then treated with the drop wise addition of a 0° C. solution of tin (II) chloride (13.0 g, 0.058 mol) in concentrated aqueous HCl (14 ml). This mixture is stirred for 15 min and then filtered. The isolated solid is washed with cold saturated aqueous NaCl and then suspended in 50% NaOH. The resultant slurry is diluted with H$_2$O and extracted with Et$_2$O. The organic phase is dried over MgSO$_4$, filtered, and concentrated. The resulting residue is dissolved in 100 ml of Et$_2$O and cooled to 0° C. 4.0 M HCl in dioxane (15 ml) is added drop wise to this solution and the resulting precipitate collected to yield 4.58 g (81%) of the desired hydrazine hydrochloride. LC/MS calculated for C16H20FN2: 259.3 found: 259.2

Step 2: (4'-Butyl-2-fluoro-biphenyl-3-yl)-hydrazine hydrochloride from the previous step (90 mg, 0.306 mmol) and 4-Acetyl-benzamide (Sigman, M. E. et al. *J. Am. Chem. Soc.* 1988, 110, 4297.) (50 mg, 0.306 mmol) are treated with anhydrous ZnCl$_2$ (418 mg, 3.06 mmol) and acetic acid (4 mL). The reaction is heated to 105° C. for 48 hours. After cooling to room temperature, the reaction is diluted with ethyl acetate and sequentially washed with H$_2$O (5×), 1N aqueous HCl, and saturated aqueous NaCl. The organics are then dried over Na$_2$SO$_4$ and filtered. After concentration, the crude product is purified by preparative RP LC-MS to give 4-[6-(4-Butyl-phenyl-7-fluoro-1H-indol-2-yl]-benzamide as a tan solid: $^1$H NMR (400 MHz, Acetone-d$_6$) δ 11.11 (bs, 1H), 8.08-8.01 (m, 4H), 7.59-7.43 (m, 4H), 7.38-7.29 (m, 2H), 7.18-7.12 (m, 2H), 6.65 (bs, 1H), 2.74-2.63 (m, 2H), 1.76-1.64 (m, 2H), 1.50-1.38 (m, 2H), 1.04-0.93 (m, 3H); ESMS m/z 387.2 (M+H$^+$).

Example 3

4-[7-Fluoro-6-(4-fluoro-3-methyl-phenyl)-1H-indol-2-yl]-benzoic acid

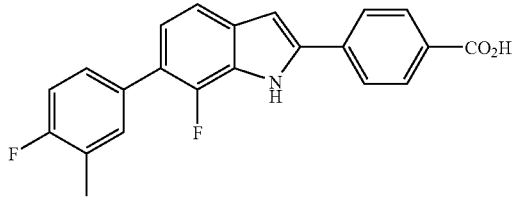

By repeating the procedures described in Example 2, using appropriate starting materials, 4-[7-Fluoro-6-(4-fluoro-3-methyl-phenyl)-1H-indol-2-yl]-benzoic acid is obtained as a white solid: $^1$H NMR (400 MHz, CD$_3$OD) δ 8.09 (d, 2H), 7.98 (d, 2H), 7.52-7.42 (m, 3H), 7.18-7.05 (m, 3H), 2.32 (s, 3H); ESMS m/z 364.1 (M+H$^+$).

Example 4

4-[7-Fluoro-6-(4-fluoro-3-methyl-phenyl)-1H-indol-2-yl]-benzenesulfonamide

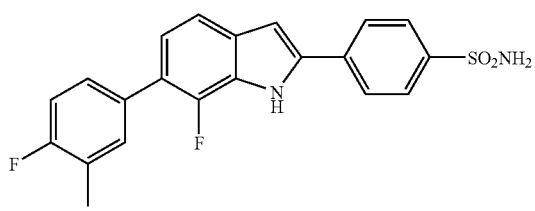

By repeating the procedures described in Example 2, using appropriate starting materials, 4-[7-Fluoro-6-(4-fluoro-3-methyl-phenyl)-1H-indol-2-yl]-benzenesulfonamide is obtained as a tan solid: $^1$H NMR (400 MHz, Acetone-d$_6$) δ

11.12 (bs, 1H), 8.18-8.13 (m, 2H), 8.06-7.98 (m, 2H), 7.59-7.48 (m, 3H), 7.22-7.12 (m, 3H), 6.68 (bs, 2H), 2.33 (s, 3H); ESMS m/z 399.1 (M+H$^+$).

Example 5

4-[6-(4-Butyl-phenyl)-3-ethyl-7-fluoro-1H-indol-2-yl]-2-hydroxy-benzoic acid

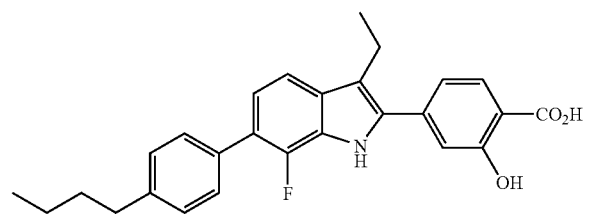

Step 1: 2-Hydroxy-4-iodo-benzoic acid

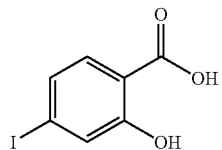

A sample of 4-amino-2-hydroxysalicylic acid (10 g, 65.3 mmol) is charged to a 2 liter Erlenmeyer flask equipped with a large stir bar, cooled in an ice/water bath and treated with concentrated sulfuric acid (20 mL) and enough water to make a free flowing suspension (~50 mL). After stirring for 20 minutes, the reaction is treated with a solution of sodium nitrite (4.55 g, 66.0 mmol) in water (20 mL) over the course of 10 minutes. After stirring an additional 3 minutes, the reaction is treated with a solution of potassium iodide (16.9 g, 101 mmol) in water (30 mL) over the course of 15 minutes. The cooling bath is removed and the reaction is carefully monitored and stirred as it generates a significant amount of nitrogen gas. After the reaction subsides, it is briefly heated to 70° C. after which it is allowed to cool to room temperature and sit overnight. The resulting solid is collected by filtration, washed with water and dried to give crude 2-hydroxy-4-iodo-benzoic acid that is used in the next reaction without further purification: ESMS m/z 265.0 (M+H$^+$).

Step 2: 2-Hydroxy-4-iodo-benzoic acid methyl ester

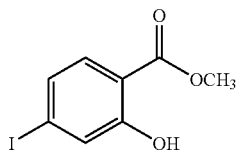

A solution of 2-hydroxy-4-iodo-benzoic acid (4.0 g, 0.015 mol) in THF (25 ml) and MeOH (25 ml) is treated by the dropwise addition of (trimethylsilyl)-diazomethane (2.0M in Et2O, 15 ml) and stirred at room temperature for 2.5 hours. Volatiles are removed in vacuo and the crude residue diluted into EtOAc. The organic phase is sequentially washed with saturated aqueous NaHCO$_3$ (3×), saturated aqueous NaCl (1×), and H$_2$O (1×). The organic phase is dried over MgSO$_4$, filtered, and concentrated. The crude product is purified with silica gel column chromatography (0-80% ethyl acetate in hexanes gradient) to afford 2-hydroxy-4-iodo-benzoic acid methyl ester: ESMS m/z 279.0 (M+H$^+$).

Step 3: 2-Hydroxy-4-vinyl-benzoic acid methyl ester

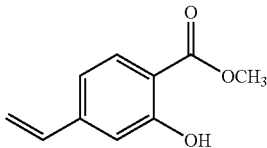

A solution of 2-hydroxy-4-iodo-benzoic acid methyl ester (8.01 g, 0.0288 mol) in THF (184 ml) and H$_2$O (46 ml) is treated with vinyl-boronic acid di-butyl ester (9.53 ml, 0.0432 mol, 1.5 eq.), NaCO$_3$ (21.37 g, 0.201 mol, 7 eq.), and dichloro-bis(triphenyl-phosphine)palladium (1.01 g, 1.44 mmol, 5 mol %). The solution is purged with N$_2$ (g) for 5 minutes and then heated to reflux for 2 hour. The reaction is concentrated in vacuo, diluted with EtOAc, and sequentially washed with H$_2$O and saturated aqueous NaCl. The organic phase is dried over MgSO$_4$, filtered, and concentrated. The crude product is purified with silica gel column chromatography (5% ethyl acetate in hexanes) to afford 2-hydroxy-4-vinyl-benzoic acid methyl ester: ESMS m/z 179.1 (M+H$^+$).

Step 4: 4-Formyl-2-hydroxy-benzoic acid methyl ester

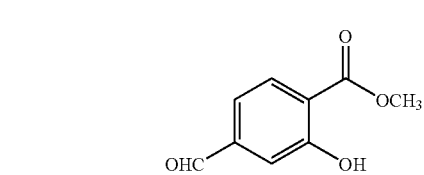

A steady stream of O$_2$ (g) is passed through a cold (−78° C.) solution of 2-hydroxy-4-vinyl-benzoic acid methyl ester (3.28 g, 0.0184 mol) in CH$_2$Cl$_2$ (50 ml). After 5 minutes, O$_3$ (g) is bubbled into the solution until the solution's color turns blue/gray. The solution is then purged with O$_2$ (g) for 5 minutes, treated with DMS (4.05 ml, 0.0552 mol) and allowed to warm to room temperature overnight. All volatiles are removed in vacuo and the crude product is purified with silica gel column chromatography (0-100% ethyl acetate in hexanes gradient) to afford 4-formyl-2-hydroxy-benzoic acid methyl ester: ESMS m/z 181.0 (M+H$^+$).

Step 5: 2-hydroxy-4-(1-hydroxy-butyl)-benzoic acid methyl ester

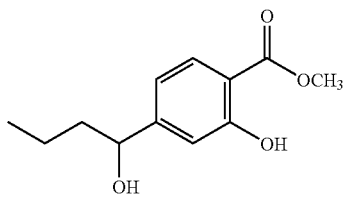

4-Formyl-2-hydroxy-benzoic acid methyl ester (360 mg, 2 mmol) is dissolved in THF (anhydrous, 10 mL). The solution is cooled to −78° C. and stirred under nitrogen. To this solution is added n-propyl-magnesium chloride (2M in THF, 2 mL, 2 mmol) dropwise via syringe. The reaction mixture is stirred at −78° C. for 1 hour, then gradually warmed to room temperature over 1 hour after which point, the reaction is quenched by adding saturated aqueous ammonium chloride. The resulting mixture is extracted with EtOAc (3×15 mL). The combined organic phase is washed with saturated aqueous NaCl and dried over $Na_2SO_4$. After concentration, the crude product is purified with silica gel flash column chromatography (10-20% ethyl acetate in hexanes gradient) to afford 2-hydroxy-4-(1-hydroxy-butyl)-benzoic acid methyl ester as a colorless oil: $^1H$ NMR (400 MHz, $CDCl_3$) δ 10.74 (s, 1H), 7.79 (d, 1H, J=8.4 Hz), 6.95 (d, 1H, J=1.2 Hz), 6.86 (dd, 1H, J=1.6, 8 Hz), 4.67 (t, 1H, J=6.8 Hz), 3.94 (s, 3H), 1.82 (br, 1H), 1.80-1.62 (m, 1H), 1.46-1.28 (m, 2H), 0.93 (t, 3H, J=7.2 Hz).

Step 6: 4-butyryl-2-hydroxy-benzoic acid methyl ester

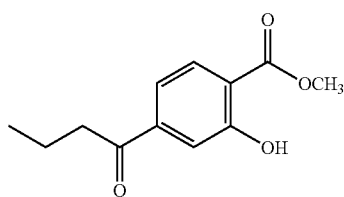

To the solution of 2-hydroxy-4-(1-hydroxy-butyl)-benzoic acid methyl ester (132 mg, 0.59 mmol) in DCM (6 mL), is added PDC (245 mg, 1.1 mmol) in one portion. The reaction is stirred overnight. The reaction mixture is filtered through a silica gel plug using DCM as eluent. The filtrate is concentrated to give 4-butyryl-2-hydroxy-benzoic acid methyl ester as a white solid: $^1H$ NMR (400 MHz, $CDCl_3$) δ 10.77 (s, 1H), 7.92 (d, 1H, J=8.4 Hz), 7.52 (d, 1H, J=1.6 Hz), 7.44 (dd, 1H, J=1.6, 8 Hz), 3.99 (s, 3H), 2.93 (t, 2H, J=7.2 Hz), 1.76 (qt, 2H, J=7.6 Hz), 1.00 (t, 3H, J=7.6 Hz).

Step 7: 4-(6-chloro-3-ethyl-7-fluoro-1H-indol-2-yl)-2-hydroxy-benzoic acid methyl ester

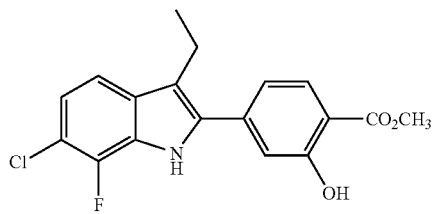

A mixture of 4-butyryl-2-hydroxy-benzoic acid methyl ester (60 mg, 0.27 mmol), (3-chloro-2-fluoro-phenyl)-hydrazine (Apollo Scientific, Ltd., 54 mg, 0.27 mmol), and zinc chloride (110 mg, 0.8 mmol) in acetic acid (2 mL) is purged with nitrogen for 5 minutes and then heated in a sealed tube at 120° C. for 2 hours. The mixture is cooled to room temperature and diluted with ethyl acetate. The resulting mixture is sequentially washed with saturated aqueous $Na_2CO_3$ and saturated aqueous NaCl, and finally dried over sodium sulfate. After concentration, the crude product is purified via silica gel flash column chromatography (10% ethyl acetate in hexanes) to afford 4-(6-chloro-3-ethyl-7-fluoro-1H-indol-2-yl)-2-hydroxy-benzoic acid methyl ester as a light yellow solid: ESMS m/z 348.1 (M+H$^+$).

Steps 8 and 9: To a mixture of 4-(6-chloro-3-ethyl-7-fluoro-1H-indol-2-yl)-2-hydroxy-benzoic acid methyl ester (50 mg, 0.14 mmol), 4-n-butyl-phenylboronic acid (50 mg, 0.28 mmol), and cesium fluoride (78 mg, 0.52 mmol) in dioxane (3 mL, anhydrous) is added palladium bis(tri-tert-butyl-phosphine) (6 mg, 10 mol %). This mixture is purged with $N_2$ for 3 minutes and then heated in a sealed tube at 120° C. for 4 hours. The mixture is cooled to room temperature, filtered, and the filtrate is concentrated. The resulting residue is dissolved in ethanol/$H_2O$ (1 mL/0.1 mL) and transferred to a microwave tube. LiOH (12 mg, 0.54 mmol) is added and the mixture is heated at 120° C. for 6 minutes under microwave irradiation. The crude product mixture is filtered. After concentration of the filtrate, the crude product is purified by preparative RP LC-MS to give 4-[6-(4-butyl-phenyl)-3-ethyl-7-fluoro-1H-indol-2-yl]-2-hydroxy-benzoic acid as a yellow solid: $^1H$ NMR (400 MHz, $CD_3OD$) δ 7.96 (d, 1H, J=8.8 Hz), 7.50 (d, 2H, J=8 Hz), 7.42 (d, 1H, J=8.4 Hz), 7.24 (d, 2H, J=8 Hz), 7.21-7.20 (m, 2H), 7.10 (dd, 1H, J=8, 8 Hz), 2.95 (q, 2H, J=7.6 Hz), 2.66 (t, 2H, J=8 Hz), 1.65 (m, 2H), 1.40 (m, 2H), 1.34 (t, 3H, J=7.6 Hz), 0.97 (t, 3H, J=7.6 Hz); ESMS m/z 432.2 (M+H$^+$).

Example 6

4-[6-(4-butyl-phenyl)-7-fluoro-3-isopropyl-1H-indol-2-yl]-2-hydroxy-benzoic acid

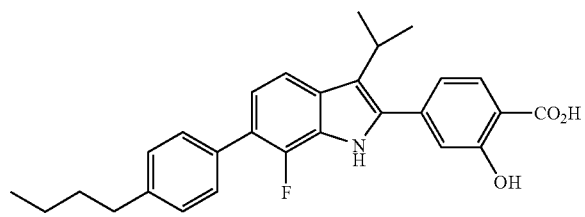

By repeating the procedures described in Example 5, using appropriate starting materials, 4-[6-(4-butyl-phenyl)-7-fluoro-3-isopropyl-1H-indol-2-yl]-2-hydroxy-benzoic acid is obtained as a yellow solid: $^1H$ NMR (400 MHz, acetone-$d_6$) δ 10.64 (s, 1H), 8.01 (d, 1H, J=8.4 Hz), 7.68 (d, 1H, J=8 Hz), 7.55 (d, 2H, J=7.6 Hz), 7.31 (d, 2H, J=8 Hz), 7.23-7.13 (m, 3H), 3.46 (m, 1H), 2.68 (t, 2H, J=7.6 Hz), 1.66 (m, 2H), 1.51 (d, 6H, J=7.2 Hz), 1.40 (m, 2H), 0.96 (t, 3H, J=7.6 Hz); ESMS m/z 446.2 (M+H$^+$).

Example 7

4-[6-(4-Butyl-phenyl)-7-fluoro-1H-indol-2-yl]-2-hydroxy-benzoic acid

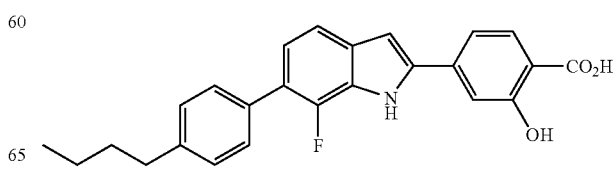

By repeating the procedures described in Example 5, using appropriate starting materials, 4-[6-(4-butyl-phenyl)-7-fluoro-1H-indol-2-yl]-2-hydroxy-benzoic acid is obtained as a yellow solid: $^1$H NMR (400 MHz, acetone-$d_6$) δ 11.12 (bs, 1H), 7.99 (d, 1H), 7.60-7.53 (m, 4H), 7.48 (d, 1H), 7.32 (d, 2H), 7.18-7.10 (m, 2H), 2.67 (t, 2H), 1.72-1.61 (m, 2H), 1.49-1.37 (m, 2H), 0.98 (t, 3H); ESMS m/z 404.2 (M+H$^+$).

Example 8

4-[6-(4-Butyl-phenyl)-7-fluoro-3-methyl-1H-indol-2-yl]-2-hydroxy-benzoic acid

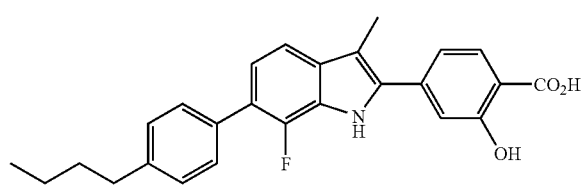

By repeating the procedures described in Example 5, using appropriate starting materials, 4-[6-(4-butyl-phenyl)-7-fluoro-3-methyl-1H-indol-2-yl]-2-hydroxy-benzoic acid is obtained as a pale yellow solid: $^1$H NMR (400 MHz, acetone-$d_6$) δ 10.75 (bs, 1H), 8.02 (d, 1H), 7.57-7.15 (m, 8H), 2.74-2.62 (m, 2H), 2.58 (s, 3H), 1.71-1.61 (m, 2H), 1.43-1.35 (m, 2H), 0.98 (t, 3H); ESMS m/z 418.2 (M+H$^+$).

Example 9

4-[6-(4-Butyl-phenyl)-1H-benzoimidazol-2-yl]-benzoic acid

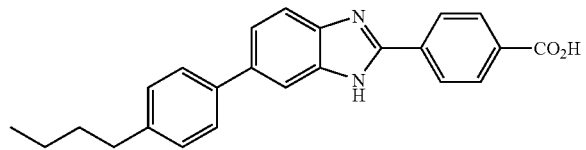

Step 1: 4'-Butyl-3-nitro-biphenyl-4-ylamine

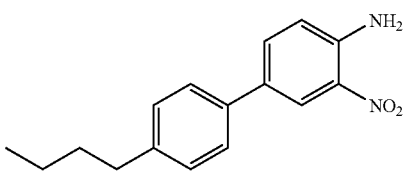

A Smith Process Vial charged with 4-bromo-2-nitroaniline (205 mg, 0.945 mmol), 4-butyl phenyl boronic acid (336 mg, 1.89 mmol), cesium fluoride (430 mg, 2.83 mmol), bis(tri-t-butyl-phosphine)-palladium (24.1 mg, 0.0472 mmol), and dioxane (2 ml) is purged with Argon (g) for 5 minutes and then heated in a microwave to 120° C. for 15 minutes. The crude reaction is filtered through Celite using EtOAc as eluent. The filtrate is concentrated in vacuo and the crude product is purified with silica gel flash column chromatography (0-100% ethyl acetate in hexanes gradient) to afford 4'-butyl-3-nitro-biphenyl-4-ylamine: ESMS m/z 271.2 (M+H$^+$).

Step 2: 4'-Butyl-biphenyl-3,4-diamine

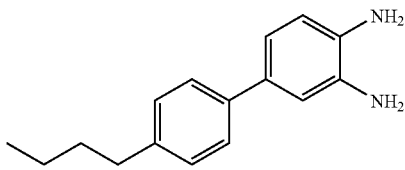

4'-Butyl-3-nitro-biphenyl-4-ylamine (117 mg, 3.70 mmol) and 10% Pd/C (10 mg) in 2:1 v/v MeOH/EtOAc (4 ml) is treated to a steady bubbling of H$_2$ (g) for 15 minutes. The reaction is kept under 1 atm of H$_2$ for 1 hour with stirring. The reaction is filtered through Celite and the filtrate concentrated in vacuo to afford 4'-butyl-biphenyl-3,4-diamine: ESMS m/z 241.2 (M+H$^+$).

Step 3: A hot (140° C.) mixture of 4-formyl-benzoic acid methyl ester (21.0 mg, 0.129 mmol) and NaHSO$_3$ (20.1 mg, 0.193 mmol, 1.5 eq.) in DMA (250 μL) is treated with the dropwise addition of 4'-butyl-biphenyl-3,4-diamine (31 mg, 0.129 mmol) in DMA (100 μL) over 10 minutes. The resulting mixture is stirred for 1 hour at 140° C. and is then treated with H$_2$O (1 ml) and stirred an additional hour. The reaction is diluted with EtOAc and the phases separated. The organic phase is dried over MgSO$_4$, filtered, and concentrated. The crude benzimidazole product is diluted with 95% Ethanol (0.5 ml) and THF (1 ml) and transferred into a Smith-Process Vial containing LiOH (15.4 mg, 0.645 mmol, 5 eq.). The reaction vessel is heated to 165° C. under microwave irradiation for 5 minutes. After concentration, the crude product is purified by preparative RP LC-MS to give 4-[6-(4-butyl-phenyl)-1H-benzoimidazol-2-yl]-benzoic acid: $^1$H NMR (400 MHz, CD$_3$OD) δ 9.00 (d, J=8.2 Hz, 1H), 8.91 (d, J=8.1 Hz, 1H), 8.63 (s, 1H), 8.53 (s, 1H), 8.31 (d, J=7.6 Hz, 2H), 8.23 (d, J=8.3 Hz, 1H), 8.02 (d, J=7.7 Hz, 1H), 7.94 (s, 1H), 7.84 (s, 1H), 7.62 (d, J=7.7 Hz, 1H), 7.33 (d, J=7.6 Hz, 1H), 3.38 (dd, J=7.8, 7.7 Hz, 1H), 2.69 (dd, J=7.8, 7.6 Hz, 1H), 2.35 (m, 1H), 2.09 (m, 1H), 1.66 (dd, J=7.4, 7.3 Hz, 3H), 1.41 (m, 1H), 0.97 (dd, J=7.3, 6.9 Hz, 2H); ESMS m/z 371.2 (M+H$^+$).

Example 10

4-[6-(4-Butyl-phenyl)-1H-benzoimidazol-2-yl]-2-hydroxy-benzoic acid

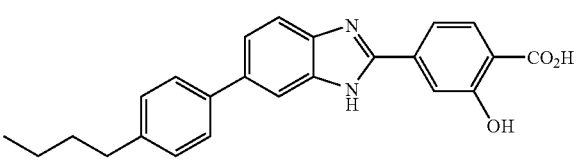

By repeating the procedures described in Example 5 and 9, using appropriate starting materials, 4-[6-(4-butyl-phenyl)-1H-benzoimidazol-2-yl]-2-hydroxy-benzoic acid is obtained: ESMS m/z 387.1 (M+H$^+$).

Example 11

N-{4-[6-(4-Butyl-phenyl)-7-fluoro-1H-indol-2-yl]-phenyl}-methanesulfonamide

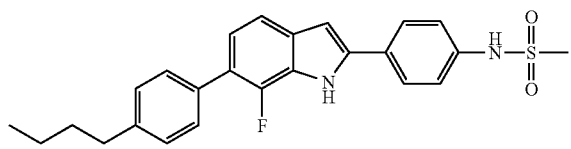

By repeating the procedures described in Example 2, using appropriate starting materials, N-{4-[6-(4-Butyl-phenyl)-7-fluoro-1H-indol-2-yl]-phenyl}-methanesulfonamide is obtained as a tan solid: $^1$H NMR (400 MHz, Acetone-$d_6$) δ 11.00 (bs, 1H), 8.79 (s, 1H), 7.99 (d, 2H), 7.55 (d, 2H), 7.52-7.44 (m, 3H), 7.32 (d, 2H), 7.15 (dd, 1H), 7.01 (s, 1H), 3.09 (s, 3H), 2.72 (t, 2H), 1.75-1.64 (m, 2H), 1.47-1.36 (m, 2H), 0.99 (t, 3H); ESMS m/z 437.2 (M+H$^+$).

Example 12

N-{4-[6-(4-Butyl-phenyl)-7-fluoro-1H-indol-2-yl]-phenyl}-acetamide

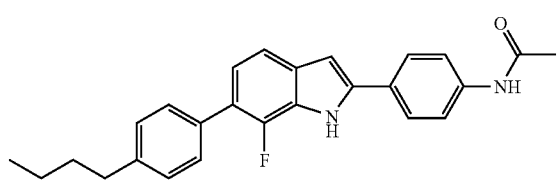

By repeating the procedures described in Example 2, using appropriate starting materials, N-{4-[6-(4-Butyl-phenyl)-7-fluoro-1H-indol-2-yl]-phenyl}-acetamide is obtained as a tan solid: $^1$H NMR (400 MHz, Acetone-$d_6$) δ 10.95 (bs, 1H), 9.32 (bs, 1H), 7.92 (d, 2H), 7.81 (d, 2H), 7.57 (d, 2H), 7.43 (d, 1H), 7.32 (d, 2H), 7.16 (dd, 1H), 6.97 (s, 1H), 2.70 (t, 2H), 1.69-1.62 (m, 2H), 1.42-1.33 (m, 2H), 0.96 (t, 3H); ESMS m/z 401.1 (M+

Example 13

N-{4-[6-(4-Butyl-phenyl)-7-fluoro-1H-indol-2-yl]-2-chloro-phenyl}-acetamide

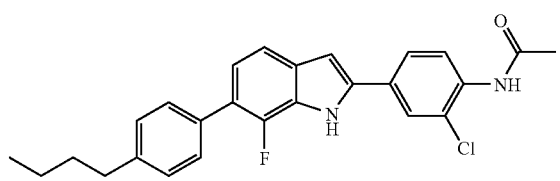

By repeating the procedures described in Example 2, using appropriate starting materials, N-{4-[6-(4-Butyl-phenyl)-7-fluoro-1H-indol-2-yl]-2-chloro-phenyl}-acetamide is obtained as a solid: $^1$H NMR (400 MHz, DMSO-$d_6$) δ 10.91 (s, 1H), 8.62 (s, 1H), 8.19 (d, J=8.6 Hz, 1H), 7.92 (d, J=2.1 Hz, 1H), 7.77 (dd, J=8.6, 2.1 Hz, 1H), 7.42 (dd, J=8.1, 1.6 Hz, 2H), 7.32 (d, J=8.2 Hz, 1H), 7.19 (d, J=8.2 Hz, 1H), 7.03 (dd, J=8.1, 6.9 Hz, 1H), 6.91 (dd, J=3.3, 2.3 Hz, 1H), 2.56 (t, J=7.7 Hz, 2H), 2.11 (s, 3H), 1.54 (m, 2H), 1.28 (m, 2H), 0.83 (t, J=7.3 Hz, 3H); ESMS m/z 435.2 (M+H$^+$).

Example 14

4-[6-(4-Butyl-phenyl)-7-fluoro-1H-indol-2-yl]-2-chloro-phenylamine

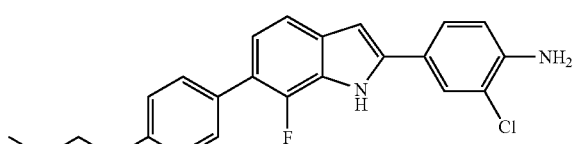

By repeating the procedures described in Example 2, using appropriate starting materials, 4-[6-(4-Butyl-phenyl-7-fluoro-1H-indol-2-yl]-2-chloro-phenylamine is obtained as a solid: ESMS m/z 393.3 (M+H$^+$).

Example 15

2-Amino-4-[6-(4-butyl-phenyl)-7-fluoro-1H-indol-2-yl]-benzoic acid

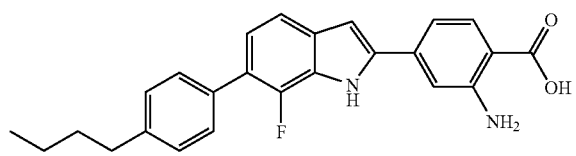

Step 1: 1-(3-Nitro-4-vinyl-phenyl)-ethanone

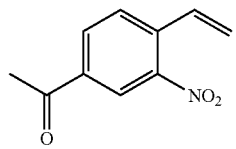

To a mixture of 4'-bromo-3'-nitroacetophenone (600 mg, 2.46 mmol), vinylboronic acid dibutyl ester (680 mg, 3.69 mmol), and sodium carbonate (1.83 g, 17.22 mmol) in THF/H$_2$O (12 mL/4 mL) is added dichlorobis(triphenylphospine) palladium (II) (86 mg, 5% mmol). The reaction tube is sealed and the mixture is purged with N$_2$ for 3 min and heated at 70° C. for 1.5 h. Then the mixture is cooled to room temperature and poured into saturated ammonia chloride aqueous solution. The mixture is extracted with ethyl acetate (3×20 mL). The organic extracts are combined, washed with brine and concentrated. The crude product is purified with silica gel column chromatography (20% ethyl acetate in hexanes) to afford 1-(3-Nitro-4-vinyl-phenyl)-ethanone as a yellow solid, 87% yield: ESMS m/z 192.0 (M+H$^+$).

Step 2: 4-Acetyl-2-nitro-benzoic acid methyl ester

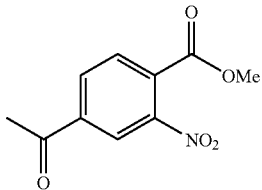

1-(3-Nitro-4-vinyl-phenyl)-ethanone obtained from the previous step (410 mg, 2.14 mmol) is dissolved in DCM (20 mL) and cooled to −78° C. NaOH (429 mg, 10.7 mmol) in MeOH (5 mL) is added. $O_3$ (g) is bubbled into the solution until the solution's color turns blue/gray. The solution is then purged with $N_2$ (g) until the blue color disappears. The solution is warmed to room temperature and concentrated to afford 4-acetyl-2-nitro-benzoic acid methyl ester as a colorless oil: $^1$H NMR (400 MHz, $CDCl_3$) δ 8.41 (d, 1H, J=1.6 Hz), 8.19 (dd, 1H, J=7.6, 1.6 Hz), 7.79 (d, 1H, J=8 Hz), 3.91 (s, 3H), 2.66 (s, 3H).

Steps 3-5: Following the procedure described in Example 2, samples of 4-acetyl-2-nitro-benzoic acid methyl ester (obtained from the previous step) and (4'-butyl-2-fluoro-biphenyl-3-yl)-hydrazine hydrochloride (Example 2, Step 1) are used to form 4-[6-(4-Butyl-phenyl)-7-fluoro-1H-indol-2-yl]-2-nitro-benzoic acid methyl ester. Hydrogenation of the nitro group to the corresponding amine (1 atm $H_2$, Pd/C) followed by saponification of the methyl ester with NaOH (EtOH/$H_2O$) and final purification using preparative RP LC-MS affords 2-Amino-4-[6-(4-butyl-phenyl)-7-fluoro-1H-indol-2-yl]-benzoic acid as a solid: $^1$H NMR (400 MHz, Acetone-$d_6$) δ 11.07 (s, 1H), 7.92 (d, 1H), 7.53 (dd, 2H), 7.45 (d, 1H), 7.36 (d, 1H), 7.31 (d, 2H), 7.19-7.13 (m, 2H), 7.02-7.00 (m, 1H), 2.67 (t, 2H), 1.67-1.62 (m, 2H), 1.42-1.37 (m, 2H), 0.94 (t, 3H); ESMS m/z 403.1 (M+H$^+$).

Assays

Compounds of the present invention are assayed to measure their potency as mimetics of TPO in an in vitro proliferation assay using the murine BaF3 cell line transfected with human TPO receptor (TPO-R):

Luciferase Reporter Assays

Ba/F3-TpoR cells are washed and resuspended in RPMI-1640 supplemented with 1% or 20% of FBS, MS, HS or (human serum albumin+alpha1 acid glycoprotein), 1% Pen-Strep-Glu and 1 mM or 25 μM $ZnSO_4$ at 8×104 cells/mL and dispensed to 384-well plates at 50 mL/well for overnight starvation (18-20 hr). The $2^{nd}$ day, the starved cells are treated with 0.5 mL of DMSO, compound or rhTpo (30 ng/mL) at 37° C., 5% $CO_2$ for 7 hours. Perkin Elmer Britelite (25 mL) diluted to 60% in water is added to each well and a few minutes later, the plates are read on a CLIPR to record the luminescence signal.

Proliferation Assay

Ba/F3-TPO-R cells are washed and resuspended in RPMI-1640 supplemented with 1% FBS, 1% Pen-Strep-Glu and 1 mM or 25 μM $ZnSO_4$ at 8×104 cells/mL and dispensed at 50 mL/well for overnight starvation (18-20 hours). The $2^{nd}$ day, the starved cells are treated with 0.5 mL of DMSO, compound or rhTpo (30 ng/mL) at 37° C., 5% $CO_2$ for 48 hours. Alamar Blue reagent (3.5 μL at ~7% final concentration) is added to each well, the plates are incubated for 4 hours and read on an Analyst GT to record the fluorescence signal.

CFU-Meg Assay

CD34+ cells and MegaCult-C kit (StemCell Technologies, Inc., Vancouver, Canada) are used for the assay. CD34+ cells are mixed with the MegaCult-C collagen solution according to the manufacturer's protocol at 104 cells per slide. After addition of TPO or a compound of the invention at different concentrations, the slides are incubated at 37° C., 5% $CO_2$ for 12 days, fixed, stained for human CFU-Meg and colonies are quantitated using an inverted microscope.

Compounds of Formula I, in free form or in pharmaceutically acceptable salt form, exhibit valuable pharmacological properties, for example, as indicated by the in vitro tests described in this application. The compounds of the invention preferably exhibit TPO mimetic activity with an IC50 in the range of $1\times10^{-9}$ to $1\times10^{-5}$M, preferably less than 500 nM, more preferably less than 250 nM. Compounds of Formula I exhibit efficacy in the range of 25% to 150% relative to TPO.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula (Ia):

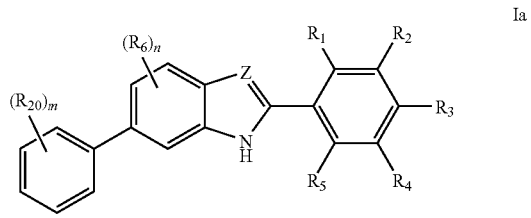

in which:
n is selected from 0, 1, 2 and 3;
m is selected from 0, 1, 2, 3, 4 and 5;
Z is $CR_8$; wherein $R_8$ is selected from hydrogen, halo, $C_{1-6}$alkyl, halo-substituted-$C_{1-6}$alkyl; wherein any alkyl of $R_8$ can optionally have a methylene replaced by an atom or group selected from —S(O)$_{0-2}$—, —C(O)—, —NR$_9$— and —O—; wherein $R_9$ is selected from hydrogen and $C_{1-6}$alkyl;
$R_1$, $R_2$, $R_4$ and $R_5$ are independently selected from hydrogen, halo, hydroxy, nitro, —XNR$_9$R$_{10}$, $C_{1-6}$alkyl, and halo-substituted-$C_{1-6}$alkyl; wherein X is selected from a bond and $C_{1-6}$alkylene; and $R_9$ and $R_{10}$ are independently is selected from hydrogen and $C_{1-6}$alkyl;
$R_3$ is selected from —C(O)OR$_{11}$, —C(O)NR$_{11}$R$_{12}$, —NR$_{11}$S(O)$_2$R$_{12}$, —S(O)$_2$NR$_{11}$R$_{12}$, —NR$_{11}$C(O)R$_{12}$, —NR$_{11}$C(O)NR$_{11}$R$_{12}$, —NR$_{11}$R$_{12}$, —NR$_{11}$C(O)C(O)OR$_{12}$ and —NR$_{11}$C(O)OR$_{12}$; wherein $R_{11}$ and $R_{12}$ are independently selected from hydrogen, $C_{1-6}$alkyl, halo-substituted-$C_{1-6}$alkyl, $C_{1-6}$alkoxy, cyano-$C_{1-6}$alkyl, hydroxy-$C_{1-6}$alkyl and $C_{1-6}$alkyl substituted with —NR$_9$R$_{10}$; and wherein when $R_3$ is —C(O)OR$_{11}$, or C(O)NR$_{11}$R$_{12}$, then $R_{11}$ and $R_{12}$ are independently selected from hydrogen and $C_{1-6}$alkyl;

$R_6$ is selected from halo and $C_{1-6}$alkyl; and
$R_{20}$ is selected from halo and $C_{1-6}$alkyl,
and the pharmaceutically acceptable salts thereof.

2. The compound of claim 1 in which $R_6$ is fluoro and $R_{20}$ is selected from fluoro, methyl and butyl.

3. The compound of claim 2 in which $R_3$ is selected from carboxyl, amino-carbonyl, amino-sulfonyl, methyl-sulfonyl-amino and amino; and $R_4$ is selected from hydrogen, hydroxyl, nitro and amino.

4. The compound of claim 3 selected from 4-[6-(4-butyl-phenyl)-7-fluoro-1H-indol-2-yl]-benzoic acid; 4-[6-(4-butyl-phenyl)-7-fluoro-1H-indol-2-yl]-benzamide; 4-[7-fluoro-6-(4-fluoro-3-methyl-phenyl)-1H-indol-2-yl]-benzoic acid; 4-[7-fluoro-6-(4-fluoro-3-methyl-phenyl)-1H-indol-2-yl]-benzenesulfonamide; 4-[6-(4-butyl-phenyl)-3-ethyl-7-fluoro-1H-indol-2-yl]-2-hydroxy-benzoic acid; 4-[6-(4-butyl-phenyl)-7-fluoro-3-isopropyl-1H-indol-2-yl]-2-hydroxy-benzoic acid; 4-[6-(4-butyl-phenyl)-7-fluoro-1H-indol-2-yl]-2-hydroxy-benzoic acid; 4-[6-(4-butyl-phenyl)-7-fluoro-3-methyl-1H-indol-2-yl]-2-hydroxy-benzoic acid; N-{4-[6-(4-Butyl-phenyl)-7-fluoro-1H-indol-2-yl]-phenyl}-methanesulfonamide; N-{4-[6-(4-Butyl-phenyl)-7-fluoro-1H-indol-2-yl]-phenyl}-acetamide; N-{4-[6-(4-Butyl-phenyl)-7-fluoro-1H-indol-2-yl]-2-chloro-phenyl}-acetamide; 4-[6-(4-Butyl-phenyl)-7-fluoro-1H-indol-2-yl]-2-chloro-phenylamine; and 2-Amino-4-[6-(4-butyl-phenyl)-7-fluoro-1H-indol-2-yl]-benzoic acid.

5. A pharmaceutical composition comprising a therapeutically effective amount of a compound of claim 1 in combination with a pharmaceutically acceptable excipient.

6. A method for treating thrombocytopenia in a subject in need thereof, wherein the method comprises administering to the subject a therapeutically effective amount of a compound of Formula (Ia) of claim 1.

\* \* \* \* \*